(12) United States Patent  (10) Patent No.: US 8,981,927 B2
McSheffrey  (45) Date of Patent: Mar. 17, 2015

(54) OBJECT TRACKING WITH EMERGENCY EQUIPMENT

(75) Inventor: Brendan T. McSheffrey, Newton, MA (US)

(73) Assignee: en-Gauge, Inc., Rockland, MA (US)

( * ) Notice: Subject to any disclaimer, the term of this patent is extended or adjusted under 35 U.S.C. 154(b) by 558 days.

(21) Appl. No.: 12/371,381

(22) Filed: Feb. 13, 2009

(65) Prior Publication Data

US 2009/0243836 A1  Oct. 1, 2009

Related U.S. Application Data

(60) Provisional application No. 61/028,245, filed on Feb. 13, 2008.

(51) Int. Cl.
| | |
|---|---|
| *G08B 1/08* | (2006.01) |
| *G08B 25/08* | (2006.01) |
| *A61N 1/39* | (2006.01) |
| *G06Q 10/08* | (2012.01) |
| *G08B 7/06* | (2006.01) |
| *G08B 25/12* | (2006.01) |

(Continued)

(52) U.S. Cl.
CPC  *G08B 25/08* (2013.01); *A61N 1/39* (2013.01); *G06Q 10/087* (2013.01); *G08B 7/062* (2013.01); *G08B 25/12* (2013.01); *G08B 29/26* (2013.01); *A62C 13/76* (2013.01)
USPC .................................. 340/539.13; 340/539.1

(58) Field of Classification Search
CPC ................................ G08B 19/00; G08B 21/00
USPC ............ 340/286.05, 506, 517, 524, 525, 531, 340/533, 539.16–539.18, 539.2, 340/539.22–539.23, 539.26–539.27, 577, 340/628, 539.13, 573.4, 56.1, 572.18, 340/539.1; 169/60, 61
See application file for complete search history.

(56) References Cited

U.S. PATENT DOCUMENTS

| | | | |
|---|---|---|---|
| 50,581 | A | 10/1865 | Henis |
| 558,643 | A | 4/1896 | Fennessy |
| 768,109 | A | 8/1904 | Ballard et al. |

(Continued)

FOREIGN PATENT DOCUMENTS

| | | |
|---|---|---|
| DE | 3731793 | 3/1989 |
| FR | 2340109 | 9/1977 |

(Continued)

OTHER PUBLICATIONS

"Exciting new Products for Measuring Flow and Pressure", Cole-Parmer Brochure Canada Apr. 23, 1996, 1 pg.

(Continued)

*Primary Examiner* — Kerri McNally
(74) *Attorney, Agent, or Firm* — Strategic Patents, P.C.

(57) ABSTRACT

A system including a network of emergency equipment stations is described. The network includes at least one emergency equipment station. The emergency equipment station includes an emergency assistance device, a first sensor configured to detect an object within a vicinity of the emergency equipment station and a second sensor configured to sense at least one selectable predetermined internal condition. The system may further include a central station that is remotely located from the emergency equipment station. The central station is configured to communicate with the emergency equipment station as well as the network and receive data from the first and the second sensors.

12 Claims, 11 Drawing Sheets

(51) Int. Cl.
   *G08B 29/26* (2006.01)
   *A62C 13/76* (2006.01)

(56) References Cited

U.S. PATENT DOCUMENTS

| | | | |
|---|---|---|---|
| 922,456 A | 5/1909 | Casey | |
| 1,825,367 A | 9/1931 | Schilling | |
| 1,950,142 A | 3/1934 | Hastings | |
| 2,189,991 A | 2/1940 | Muller | |
| 2,550,157 A | 4/1951 | Mazza | |
| 2,670,194 A | 2/1954 | Hansson | |
| 2,710,666 A | 6/1955 | May | |
| 2,920,641 A | 1/1960 | Girolo | |
| 3,145,375 A | 8/1964 | Webb | |
| 3,283,578 A | 11/1966 | Moore | |
| 3,333,641 A | 8/1967 | Hansom | |
| 3,407,665 A | 10/1968 | Noakes | |
| 3,664,430 A | 5/1972 | Sitabkhan | |
| 3,710,613 A | 1/1973 | Innes et al. | |
| 3,735,376 A | 5/1973 | Kermer et al. | |
| 3,773,145 A * | 11/1973 | Drexler | 187/277 |
| 3,946,175 A | 3/1976 | Sitabkhan | |
| 3,954,612 A | 5/1976 | Wilkerson | |
| 4,003,048 A | 1/1977 | Weise | |
| 4,015,250 A | 3/1977 | Fudge | |
| 4,034,697 A | 7/1977 | Russell | |
| 4,051,467 A | 9/1977 | Galvin | |
| 4,100,537 A | 7/1978 | Carlson | |
| 4,101,887 A | 7/1978 | Osborne | |
| 4,119,153 A | 10/1978 | Avant | |
| 4,125,084 A | 11/1978 | Salmonsen et al. | |
| 4,143,545 A | 3/1979 | Sitabkhan | |
| 4,184,377 A | 1/1980 | Hubbard | |
| 4,227,577 A * | 10/1980 | Iida | 169/61 |
| 4,246,046 A | 1/1981 | Lameyer | |
| 4,279,155 A | 7/1981 | Balkanli | |
| 4,289,207 A | 9/1981 | Wernert | |
| 4,300,311 A | 11/1981 | Marchant | |
| 4,303,395 A | 12/1981 | Bower | |
| 4,342,988 A | 8/1982 | Thompson et al. | |
| 4,360,802 A | 11/1982 | Pinto | |
| 4,384,486 A | 5/1983 | Eckert | |
| 4,418,336 A | 11/1983 | Taylor | |
| 4,419,658 A | 12/1983 | Jarosz et al. | |
| 4,436,414 A | 3/1984 | Kamiyama et al. | |
| 4,512,190 A | 4/1985 | Sledmere | |
| 4,531,114 A | 7/1985 | Topol et al. | |
| 4,548,274 A | 10/1985 | Simpson | |
| 4,586,383 A | 5/1986 | Blomquist | |
| 4,599,902 A | 7/1986 | Gray | |
| 4,613,851 A | 9/1986 | Hines | |
| 4,635,480 A | 1/1987 | Hrncir et al. | |
| 4,697,643 A | 10/1987 | Sassier | |
| 4,709,330 A * | 11/1987 | Yokoi et al. | 700/90 |
| 4,805,448 A | 2/1989 | Armell | |
| 4,823,116 A | 4/1989 | Kitchen, III et al. | |
| 4,823,788 A | 4/1989 | Smith et al. | |
| 4,833,469 A | 5/1989 | David | |
| 4,835,522 A | 5/1989 | Andrejasich et al. | |
| 4,866,423 A | 9/1989 | Anderson et al. | |
| 4,887,291 A | 12/1989 | Stillwell | |
| 4,890,677 A | 1/1990 | Scofield | |
| 4,928,255 A | 5/1990 | Brennecke et al. | |
| 4,975,687 A | 12/1990 | Murphy, Jr. et al. | |
| 4,979,572 A | 12/1990 | Mikulec | |
| 5,020,367 A | 6/1991 | White | |
| 5,027,871 A | 7/1991 | Guenther | |
| 5,072,618 A | 12/1991 | Taylor et al. | |
| 5,123,409 A | 6/1992 | Sheffield et al. | |
| 5,124,686 A | 6/1992 | White et al. | |
| 5,153,567 A | 10/1992 | Chimento | |
| 5,153,722 A | 10/1992 | Goedeke et al. | |
| 5,224,051 A | 6/1993 | Johnson | |
| 5,305,639 A | 4/1994 | Pontefract | |
| 5,339,074 A * | 8/1994 | Shindley et al. | 340/5.28 |
| 5,357,242 A | 10/1994 | Morgano et al. | |
| 5,388,570 A | 2/1995 | Wassil | |
| 5,400,246 A | 3/1995 | Wilson et al. | |
| 5,457,995 A | 10/1995 | Staton et al. | |
| 5,460,228 A | 10/1995 | Butler | |
| 5,472,012 A | 12/1995 | Wood et al. | |
| 5,475,614 A | 12/1995 | Tofte et al. | |
| 5,479,820 A | 1/1996 | Fekete | |
| 5,483,826 A | 1/1996 | Schultz et al. | |
| 5,486,811 A * | 1/1996 | Wehrle et al. | 340/522 |
| 5,534,851 A | 7/1996 | Russek | |
| 5,578,993 A | 11/1996 | Sitabkhan et al. | |
| 5,589,639 A | 12/1996 | D'Antonio et al. | |
| 5,593,426 A | 1/1997 | Morgan et al. | |
| 5,596,501 A | 1/1997 | Comer et al. | |
| 5,613,778 A | 3/1997 | Lawson | |
| 5,652,393 A | 7/1997 | Lawson | |
| 5,706,273 A | 1/1998 | Guerreri | |
| 5,728,933 A | 3/1998 | Schultz et al. | |
| 5,775,430 A | 7/1998 | McSheffrey | |
| 5,781,108 A | 7/1998 | Jacob et al. | |
| 5,793,280 A | 8/1998 | Hincher | |
| 5,808,541 A | 9/1998 | Golden | |
| 5,816,224 A | 10/1998 | Welsh et al. | |
| 5,829,465 A | 11/1998 | Garretson | |
| 5,848,651 A | 12/1998 | McSheffrey et al. | |
| 5,853,244 A | 12/1998 | Hoff et al. | |
| 5,864,287 A | 1/1999 | Evans, Jr. et al. | |
| 5,874,899 A | 2/1999 | Barmore, Jr. et al. | |
| 5,877,426 A | 3/1999 | Hay et al. | |
| 5,936,531 A * | 8/1999 | Powers | 340/628 |
| 5,952,919 A * | 9/1999 | Merrill | 340/539.18 |
| 6,014,307 A | 1/2000 | Crimmins | |
| 6,104,301 A | 8/2000 | Golden | |
| 6,114,823 A | 9/2000 | Doner et al. | |
| 6,125,940 A | 10/2000 | Oram | |
| 6,128,576 A | 10/2000 | Nishimoto et al. | |
| 6,137,417 A | 10/2000 | McDermott | |
| 6,141,584 A | 10/2000 | Rockwell et al. | |
| 6,155,160 A | 12/2000 | Hochbrueckner | |
| 6,168,563 B1 | 1/2001 | Brown | |
| 6,240,365 B1 | 5/2001 | Bunn | |
| 6,270,455 B1 | 8/2001 | Brown | |
| 6,279,664 B1 | 8/2001 | Yanovsky et al. | |
| 6,289,331 B1 | 9/2001 | Pedersen et al. | |
| 6,301,501 B1 | 10/2001 | Cronin et al. | |
| 6,302,218 B1 | 10/2001 | McSheffrey et al. | |
| 6,311,779 B2 | 11/2001 | McSheffrey et al. | |
| 6,317,042 B1 | 11/2001 | Engelhorn et al. | |
| 6,327,497 B1 | 12/2001 | Kirchgeorg et al. | |
| 6,336,362 B1 | 1/2002 | Duenas | |
| 6,351,689 B1 | 2/2002 | Carr et al. | |
| 6,357,292 B1 | 3/2002 | Schultz et al. | |
| 6,401,713 B1 | 6/2002 | Hill et al. | |
| 6,450,254 B1 | 9/2002 | Hoyle et al. | |
| 6,488,099 B2 | 12/2002 | McSheffrey et al. | |
| 6,496,110 B2 | 12/2002 | Peterson et al. | |
| 6,522,531 B1 * | 2/2003 | Quintana et al. | 361/679.03 |
| 6,529,590 B1 | 3/2003 | Centers | |
| 6,542,076 B1 | 4/2003 | Joao | |
| 6,556,981 B2 | 4/2003 | Pedersen et al. | |
| 6,567,006 B1 | 5/2003 | Lander et al. | |
| 6,585,055 B2 | 7/2003 | Mcsheffrey et al. | |
| 6,587,049 B1 | 7/2003 | Thacker | |
| 6,598,454 B2 | 7/2003 | Brazier et al. | |
| 6,646,545 B2 | 11/2003 | Bligh | |
| 6,647,762 B1 | 11/2003 | Roy | |
| 6,735,473 B2 | 5/2004 | Kolder et al. | |
| 6,766,688 B2 | 7/2004 | O'Shea | |
| 6,772,260 B2 | 8/2004 | Kawase et al. | |
| 6,853,309 B1 | 2/2005 | Schröter | |
| 6,856,251 B1 | 2/2005 | Tietsworth et al. | |
| 6,866,042 B2 | 3/2005 | Izuchukwu | |
| 7,081,815 B2 * | 7/2006 | Runyon et al. | 340/541 |
| 7,111,510 B2 | 9/2006 | Tadoa et al. | |
| 7,174,769 B2 | 2/2007 | McSheffrey, Jr. et al. | |
| 7,174,783 B2 | 2/2007 | McSheffrey, Jr. et al. | |
| 7,188,679 B2 | 3/2007 | McSheffrey et al. | |
| 7,245,030 B2 | 7/2007 | Nelson et al. | |

(56) References Cited

U.S. PATENT DOCUMENTS

| | | | |
|---|---|---|---|
| 7,271,704 B2 * | 9/2007 | McSheffrey et al. | 340/286.05 |
| 7,289,881 B2 * | 10/2007 | Ota et al. | 700/245 |
| 7,411,497 B2 * | 8/2008 | Kates | 340/556 |
| 7,450,020 B2 | 11/2008 | McSheffrey et al. | |
| 7,574,911 B2 | 8/2009 | McSheffrey et al. | |
| 7,726,411 B2 | 6/2010 | McSheffrey, Jr. et al. | |
| 7,728,715 B2 | 6/2010 | Riedel et al. | |
| 7,891,241 B2 | 2/2011 | McSheffrey et al. | |
| 7,891,435 B2 | 2/2011 | McSheffrey et al. | |
| 7,895,884 B2 | 3/2011 | McSheffrey, Jr. et al. | |
| 7,961,089 B2 | 6/2011 | McSheffrey et al. | |
| 8,009,020 B2 | 8/2011 | Riedel et al. | |
| 2001/0025713 A1 | 10/2001 | Mcsheffrey et al. | |
| 2001/0052681 A1 | 12/2001 | Deavila | |
| 2003/0071736 A1 | 4/2003 | Brazier et al. | |
| 2003/0116329 A1 | 6/2003 | McSheffrey et al. | |
| 2003/0135324 A1 | 7/2003 | Navab | |
| 2003/0189492 A1 | 10/2003 | Harvie | |
| 2004/0017471 A1 | 1/2004 | Suga et al. | |
| 2004/0113805 A1 * | 6/2004 | Fardin et al. | 340/686.2 |
| 2004/0123486 A1 | 7/2004 | Hameed et al. | |
| 2004/0200058 A1 | 10/2004 | Fish | |
| 2004/0265134 A1 | 12/2004 | Iimura et al. | |
| 2005/0006109 A1 * | 1/2005 | McSheffrey et al. | 169/75 |
| 2005/0124315 A1 | 6/2005 | Kageyama et al. | |
| 2005/0174091 A1 | 8/2005 | Dayan et al. | |
| 2005/0185606 A1 | 8/2005 | Rayment et al. | |
| 2005/0270156 A1 * | 12/2005 | Ravet | 340/572.1 |
| 2006/0027547 A1 | 2/2006 | Silvestro | |
| 2006/0036515 A1 | 2/2006 | Ingalsbe et al. | |
| 2006/0074513 A1 | 4/2006 | DeRose et al. | |
| 2006/0103520 A1 * | 5/2006 | Clark | 340/506 |
| 2006/0131393 A1 | 6/2006 | Cok et al. | |
| 2007/0050137 A1 | 3/2007 | Woon et al. | |
| 2008/0004798 A1 | 1/2008 | Troxler et al. | |
| 2008/0232604 A1 | 9/2008 | Dufresne et al. | |
| 2008/0313255 A1 | 12/2008 | Geltner et al. | |
| 2010/0171624 A1 | 7/2010 | McSheffrey et al. | |
| 2010/0192695 A1 | 8/2010 | McSheffrey et al. | |
| 2010/0245570 A1 | 9/2010 | Riedel et al. | |
| 2011/0109454 A1 | 5/2011 | Mcsheffrey, Sr. et al. | |
| 2011/0241873 A1 | 10/2011 | Mcsheffrey et al. | |
| 2011/0285847 A1 | 11/2011 | Riedel et al. | |

FOREIGN PATENT DOCUMENTS

| | | |
|---|---|---|
| FR | 2515845 | 5/1983 |
| FR | 2676931 | 12/1992 |
| WO | WO-81/02484 | 9/1981 |
| WO | WO-94/11853 | 5/1994 |
| WO | WO-01/46780 | 6/2001 |
| WO | WO-01/93220 | 12/2001 |
| WO | WO-03/076765 | 9/2003 |
| WO | WO-03/098908 | 11/2003 |

OTHER PUBLICATIONS

"Help That Comes Too Late Is As Good As No Help At All—The Fire Extinguisher Alarm System Gives Immediate Help", Invention Technologies, Inc. Press Release.

"NFPA 10 Standard for Portable Fire Extinguishers", National Fire protection Association 1998 Edition , pp. 10.1-10.56.

* cited by examiner

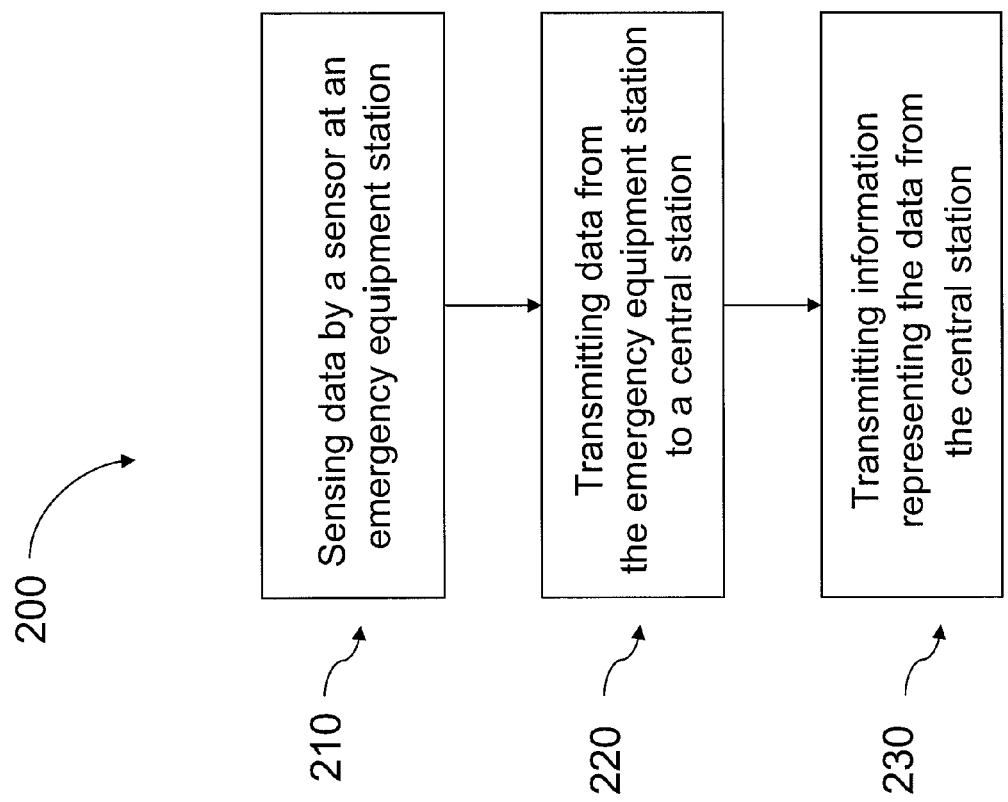

OBJECT TRACKING WITH EMERGENCY EQUIPMENT

RELATED APPLICATION

Pursuant to 35 U.S.C. §119(e), this application claims the benefit of prior U.S. provisional application 61/028,245, filed Feb. 13, 2008, which is incorporated by reference in its entirety.

TECHNICAL FIELD

This description relates sensing objects (e.g., people, equipment, packages, etc.) with emergency equipment stations and transmitting information representative of the detected objects to a control station for tracking the objects.

BACKGROUND

Functionality of emergency equipment stations has been expanding rapidly. Various monitoring techniques and methodologies are being incorporated in the emergency equipment stations to improve their performance.

SUMMARY

The specification describes technology related to communicating information in a network of emergency equipment stations.

In general, in one aspect, the specification describes a system for communicating information. The system includes a network of emergency equipment stations. The network includes at least one emergency equipment station. The emergency equipment station includes an emergency assistance device, a first sensor configured to detect an object within a vicinity of the emergency equipment station and a second sensor configured to sense at least one selectable predetermined internal condition. The system may further include a central station that is remotely located from the emergency equipment station. The central station is configured to communicate with the emergency equipment station as well as the network and receive data from the first and the second sensors.

These and other implementations can optionally include one or more of the following features. The system may include at least one receiver that is remotely located from the central station and configured to receive information from the central station. The receiver may be deployed in a building, a vehicle or as part of a hand-held device. The second sensor may be configured to sense an ambient temperature. The central station may be configured to identify a location of the object to the receiver. In some implementations, the first sensor may be configured to sense a movement of the object. The emergency assistance device may include any combination of a fire extinguisher, a fire pull alarm, an emergency lighting device and a defibrillator. The network of emergency equipment stations may include or be connected in a mesh network configuration. The emergency equipment station may also include communication circuitry configured to communicate with the central station. In some implementations, the system may further include a third sensor configured to sense a selectable predetermined external condition. The selectable predetermined external condition may include an ambient temperature, a presence of an obstruction and a removal of the emergency assistance device. In some implementations, the first sensor is configured to couple with a module of the object. The central station may be further configured to track movement of the object. The central station may also include a database to store a location of the emergency equipment station.

In general, another aspect of the subject matter described in this specification can be embodied in a method for communicating information. The method includes sensing a presence of an object by a first sensor. The method also includes sensing one or more selectable predetermined internal conditions of the emergency equipment station by a second sensor. Data sensed by the first and second sensors are transmitted from the emergency equipment station to a central station by way of a network of emergency equipment stations. The method further includes transmitting information representing the data by the central station to at least one receiver remotely located to the central station.

These and other implementations can optionally include one or more of the following features. The sensing by the first sensor may be provided, at least in part, by a mutual coupling between the first sensor and an identification module of the object. In some implementations, the network of emergency equipment stations may be connected in a mesh configuration. The selectable predetermined internal conditions may include a pressure in a fire extinguisher and a remaining life of a part of the emergency equipment station. The method may also include sensing a selectable predetermined external condition by a third sensor. The selectable predetermined external condition may include an ambient temperature, a presence of an obstruction and a removal of an emergency assistance device.

In general, still another aspect of the subject matter described in this specification can be embodied in a system for communicating information that includes a network of emergency equipment stations. There is at least one emergency equipment station in the network. The emergency equipment station includes a plurality of sensors configured to detect an object within a vicinity of the emergency equipment station and at least one selectable predetermined condition. The system further includes a central station that is located remotely from the emergency equipment station. The central station is configured to receive data sensed by the plurality of sensors from the network of emergency equipment stations. The system also includes at least one receiver remotely located from the central station. The receiver is configured to receive information from the central station.

These and other implementations can optionally include one or more of the following features. The central station may be configured to track movement of the object. The central station may also be configured to maintain a database representative of all locations of the plurality of sensors. In some implementations, the central station is configured to produce a map of at least one of the predetermined conditions and a representation of the locations of the plurality of sensors.

The details of several implementations of various aspects of the invention are set forth in the accompanying drawings and the description below. Other features, objects, and advantages of the invention will be apparent from the description and drawings, and from the claims.

DESCRIPTION OF DRAWINGS

FIG. 11 is a flowchart representing exemplary operations in communicating information.

Like reference symbols in the various drawings indicate like elements.

DETAILED DESCRIPTION

Figure 1:
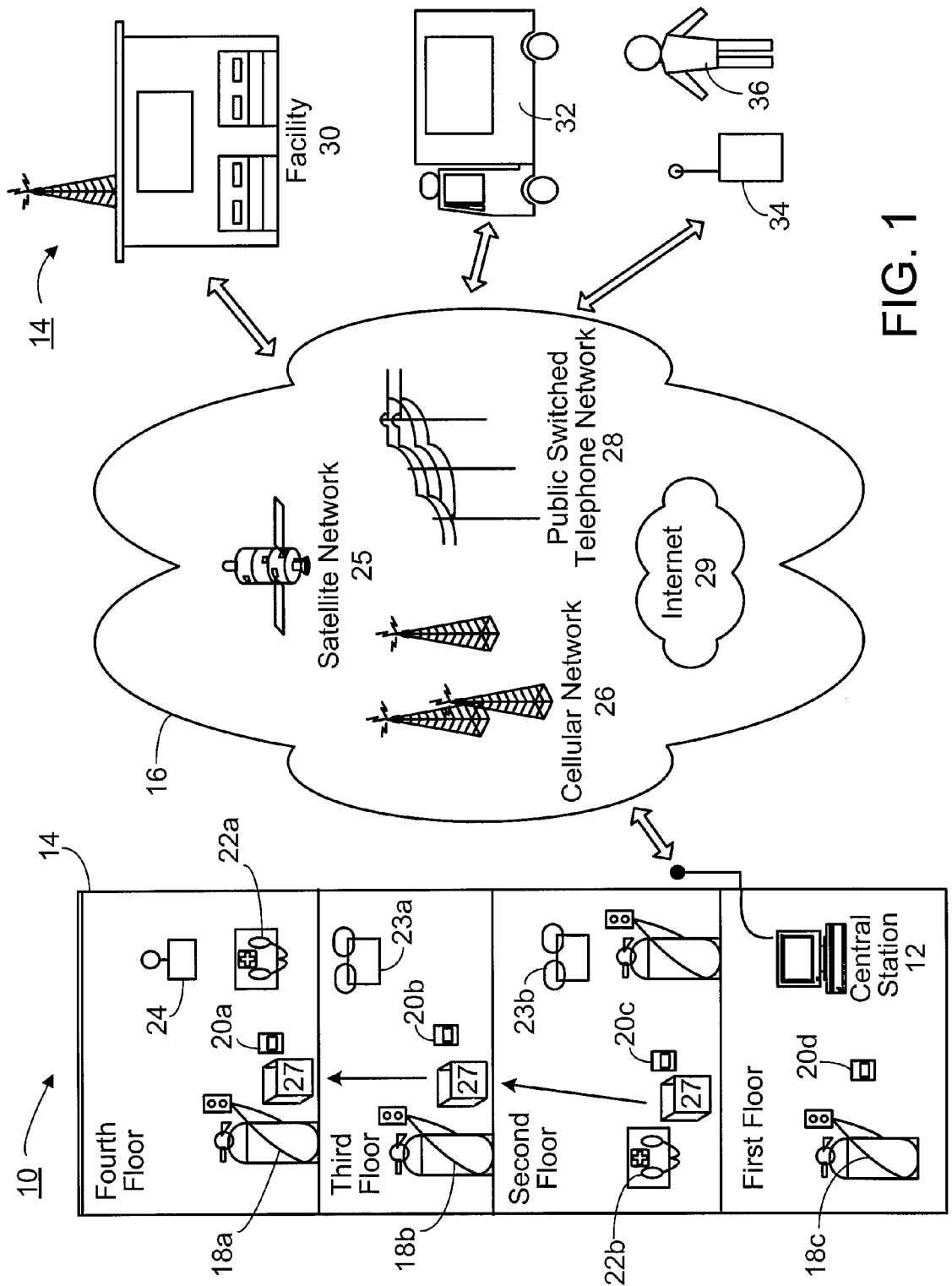
FIG. 1 is a system for communicating information collected at a network of emergency equipment stations to various locations.

Referring to FIG. 1, a system 10 for remote tracking of objects with emergency equipment includes a facility within which objects are tracked. For example, emergency equipment may be distributed throughout (e.g., in rooms, hallways, etc.) a healthcare facility (e.g., a hospital, assisted living facility, a nursing home, etc.), a commercial facility (e.g., a shopping mall, restaurant, dance club, gymnasium, etc.), an educational institution (e.g., a college campus, dormitory, etc.), a residence (e.g., a residential home, residential development, apartment complex, condominium complex, etc.), or other facility (e.g., an airport, train station, bus station, etc.). In this particular example, emergency equipment stations are distributed throughout four floors of a building 14. Each emergency equipment station includes an emergency assistance device (e.g., a fire extinguisher, fire pull alarm, emergency egress lighting, emergency lighting, defibrillator, etc.) and one or more sensors adapted to sense various internal and external conditions (e.g., ambient air temperature, presence of an obstruction blocking access to emergency assistance device, etc.). Each emergency equipment station also includes equipment (e.g. sensors) for detecting objects such as people (e.g., emergency personnel, employees, students, prisoners, etc.), packages (e.g., crates, mail parcels, etc.), equipment (e.g., vehicles associated with a facility) and other types of objects worthy of being tracked.

To process and transfer the information collected at the emergency equipment stations, system 10 includes a remote central station 12. Located in building 14, the remote central station may be in communication with other facilities (e.g., buildings), vehicles and individuals via a communication medium 16 such as a satellite network 24, cellular network 26, public switched telephone network (PSTN) 28, a computer network such as the Internet 29 or a network implemented using other networking techniques. In general, remote central station 12 remotely receives information from a network of emergency equipment stations (e.g., fire extinguisher stations 18a-18c, fire alarm pull stations 20a-20d, defibrillator stations 22a-22b, emergency lighting stations 23a-23b, and emergency egress station 24), for assisting with detecting stationary objects and tracking moving objects located and moving within the building 14. One or more techniques and methodologies may be used for detecting objects. For example, objects may be detected using infra-red sensors, radio frequency identification, sonar modules or laser scanning. In some implementations, one or more of these and other techniques may be combined to detect objects. Each emergency equipment station includes sensors and circuitry for monitoring internal and/or external conditions such as ambient air temperature, presence of an obstruction in front of the equipment, removal of the equipment from an installed position, etc. Additionally, each emergency equipment station (or device) includes sensors and circuitry for sensing and detecting objects.

Upon detection of one or more objects (e.g., a crate 27), remote central station 12 is configured to relay information about the detected object and/or external conditions to one or more destinations (e.g., another facility 30, vehicle 32, personnel 36). In some arrangements, along with detecting objects, the emergency equipment is capable of processing detection information to track the objects or to assist with tracking the objects. For example an object such as the crate 27 may be tracked while moving from the second floor to fourth floor of the building 14. The crate 27 may be tracked by collecting data on its presence at one or more locations and passing it on to the remote central station. Processing for object tracking may be partially or completely executed remote from the emergency equipment stations. For example object tracking may be executed at the remote central station 12, a separate facility (e.g the facility 30), vehicle 32 or at the location of the personnel 36. Along with object tracking, additional internal and external conditions associated with the emergency equipment stations and devices may be monitored. For example, ambient temperature may be monitored by the network of emergency equipment and remote central station 12 may be configured to transmit temperature data to destinations such as facility 30, vehicle 32 and personnel 36. By receiving this data, facilities and personnel (e.g., a fire department and emergency response personnel) can be provided with a graphical display (e.g a temperature map) of each floor of the building 14 to assist during particular events (e.g., suspected fires). In some implementations, the personnel 36 may receive the data on a handheld device 34. The handheld device 34 may include, without limitation, a wireless device such as a two way radio or a cellular device, a handheld computing device, a personal digital assistant (PDA) or a smartphone.

Various data transmission techniques and methodologies may be implemented for providing detection and tracking information to the facilities, vehicles and personnel. For example, object tracking data transmitted by remote central station 12 may be received by a communications device (e.g., dial up modem, cable modem, cellular modem, computer network interface card, etc.) at a computer at the facility 30, a computer located within the vehicle 32 (e.g., a fire truck, passenger car), and/or a hand held device 34 (e.g., a tablet computer, personal data assistant, cellular device, pager, etc.) carried by the person 36.

Bidirectional information and data transmissions may occur between on or more of the facilities and devices included in the system 10. For example, the remote central station 12 may be configured to receive data from one or more sources (e.g., facility 30, vehicle 32, handheld device 34) that may be used for various operations such as initiating diagnostic operations at one or more of the emergency equipment stations, adjusting transmission and reception parameters and protocols (e.g., operational frequency, transmission power, gain settings, etc.), etc.

Figure 2:
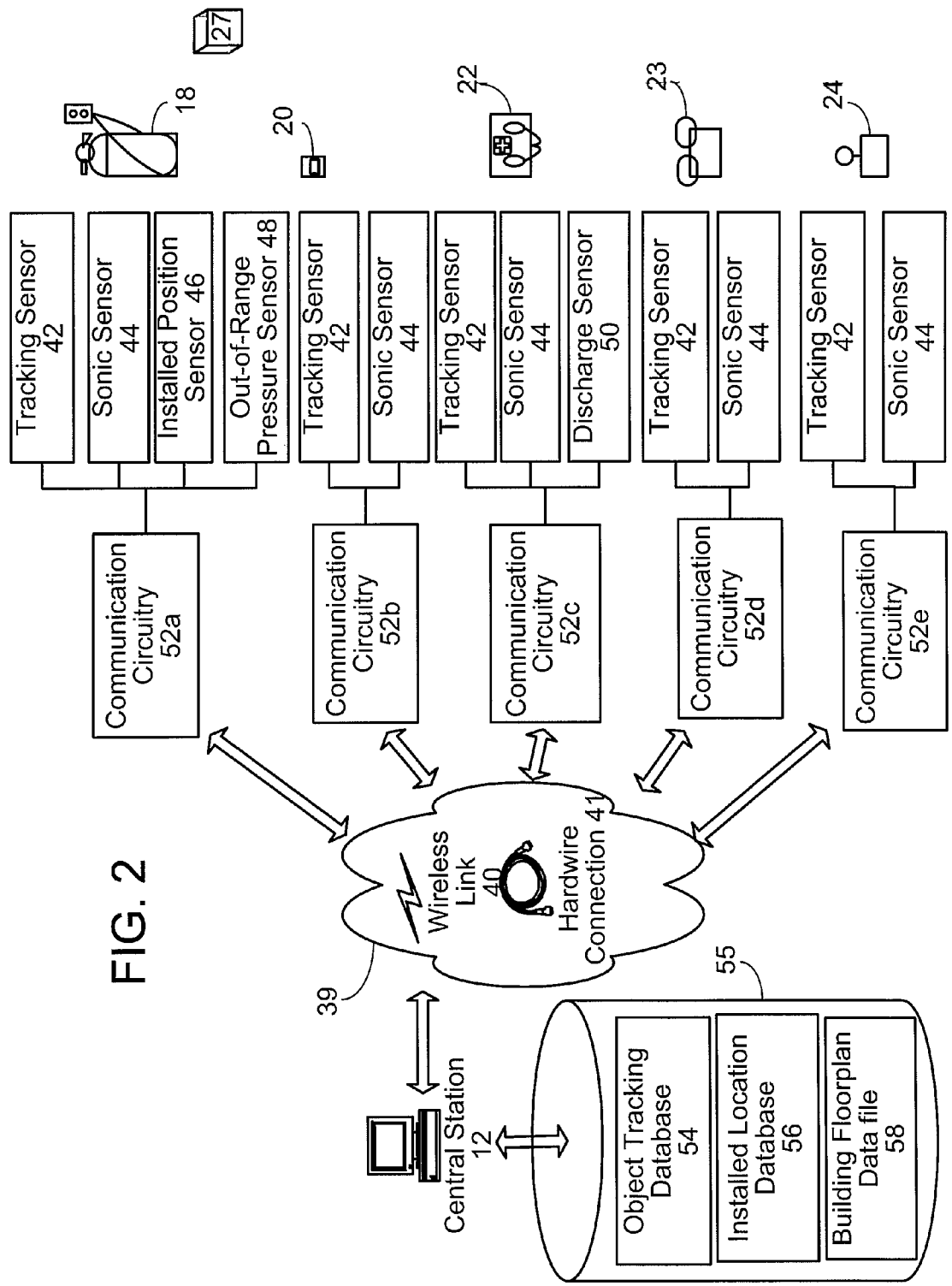
FIG. 2 is a system for collecting information sensed at various emergency equipment stations.

As shown in FIG. 2, each emergency equipment station (e.g., fire extinguisher stations 18a-18c, fire alarm pull stations 20a-20d, defibrillator stations 22a-22b, emergency lighting stations 23a-23b, and emergency egress station 24), monitors various internal and/or external conditions and is in communication with the remote central station 12 over a communication link 39 such as wireless link 40, hardwire connection 41 or a combination thereof. For an exemplary wireless communications link, a wireless repeater mesh network may be employed to relay a signal transmitted from one or more of the emergency equipment stations to the remote central station 12. As such, one or multiple emergency equipment stations may function as nodes of the mesh network.

Each emergency equipment station may include a tracking sensor 42 (although multiple tracking sensors may be implemented at a station) for detecting objects in the general vicinity of the respective station. Various types of tracking sensors may be implemented, for example, acoustic, electromagnetic, optical or other sensing techniques may be used individually or in combination. By passively or actively collecting acoustic signals emitted from objects passing within the general vicinity of a sensor, the signals may be used to identify the object (e.g., crate 27). For example, an acoustic signal unique to the object may be detected by one of the tracking sensors 42. Based upon the detection, information representative of the detection may be sent to the remote central station 12 for processing and associating the object with the location of the corresponding emergency equipment station.

Radio frequency identification (RFID) technology may also be implemented into one or more of the tracking sensors 42. In general, RFID technology uses electromagnetic and/or electrostatic coupling in the radio frequency (RF) portion of the electromagnetic spectrum to uniquely identify an object. An RFID system typically includes three components: an antenna and transceiver (often combined into one reader) and a transponder referred to as the tag. In some implementations, the antenna and the transceiver may be located at an emergency equipment station and the transponder may be located on the object 27. The antenna uses radio frequency waves to transmit a signal that activates the transponder. When activated, the tag transmits data back to the antenna, that may include information unique to the tag or may trigger such unique identification information being retrieved from a storage mechanism (e.g., memory, a storage device, etc.) or a previously retrieved file. Various electromagnetic characteristics and parameters may be implemented, for example, low frequency (e.g. 30 KHz to 500 KHz) RFID sensors that may have short transmission and detection ranges (e.g. less than ten feet) and relatively higher frequency (e.g. 850 MHz to 950 MHz and 2.4 GHz to 2.5 GHz) RFID sensors that provide longer transmission and detection ranges (e.g. greater or less than 90 feet) may be used. Other electromagnetic identification techniques may also be implemented such as bar code technology. Optical techniques and methodologies (and other tracking techniques) may also be implemented for object detection. For example, laser technology may be used to detect the presence of objects and object identification.

In addition to object detection for tracking, additional sensors may be implemented in the emergency equipment stations. For example, sensors for measuring external conditions such as ambient air temperature may also be incorporated and corresponding information from the sensors may be similarly provided to the remote central station 12. Temperature sensing may employ any known suitable temperature sensing device such as a thermocouple, thermistor etc. Other types of sensors may include ultrasonic sensors 44 for detecting the presence of an obstruction affecting access to the equipment of the corresponding emergency equipment station.

Sensors may also be incorporated that are unique to the function and type of emergency equipment housed in the station. For example, fire extinguisher station 18a-18c (18 in general) may also include a position sensor 46 to determine if the extinguisher has been removed from its installed position. An out-of-range pressure sensor 48 may detect when the pressure of fluid contained in the extinguisher is outside a predetermined pressure range. Each defibrillator station 22a-22b (22 in general) may include a discharge sensor 50 for detecting when the defibrillator is discharged. The emergency equipments and the emergency equipment stations may be of any type and form as described in the following commonly owned U.S. patents which are incorporated herein by reference: U.S. Pat. Nos. 6,585,055, 7,188,679 and 7,174,769.

Each sensor associated with each emergency equipment station is in respective communication with communication circuitry 52a-52e. In this implementation, communication circuitry 52a-52e is configured for one-way communication from the emergency equipment station to remote central station 12. In particular, communication circuitry 52a-52e is configured to continuously (or periodically) transmit to a server a signal indicating one or more detected objects (for object tracking). Upon receipt, the data is stored in database 54 or other similar structure (e.g., a data file) in storage device 55 (e.g., hard drive, CD-ROM, etc.) in communication with remote central station 12. Additionally, the installed location of each emergency equipment station may be stored in a database 56 and a floor plan of the building or buildings (where the stations are located) is also stored in data file 58 in storage device 55. In some implementations, the remote central station is provided data representing the detected object (or objects), the emergency equipment station detecting the object (or objects), the location of the emergency equipment stations, and the building floor plan. From this data, the remote central station 12 is able to assemble a graphical map of the building (or buildings) for object tracking as they transit. Such a map or other graphical display may be transmitted to one or more destinations (e.g., one or more facilities, vehicles, and personnel). In other implementations, the data from the sensors may be transmitted periodically (e.g., every 30 seconds) to remote central station 12.

Communication circuitry 52a-52e may also be configured to initiate and transmit an alarm signal to remote central station 12 upon detection of a predetermined condition by one of the sensors. For example, if sonic sensor 44 of fire extinguisher 18 detects the presence of an object obstructing access to an emergency equipment station, associated communications circuitry will initiate and transmit an alarm signal to the remote central station 12 indicating obstruction of a particular emergency equipment station. Similarly, if installed position sensor 46 detects that a fire extinguisher has been removed from its installed position or if out-of-range pressure sensor 48 detects that the internal pressure of the extinguisher is out of range (e.g., fallen below or risen above a predetermined pressure), the associated communication circuitry, e.g., communication circuitry 52a, will initiate and transmit an alarm signal to the remote central station indicating a removal of the particular fire extinguisher from its installed position or an out-of-range pressure condition. Likewise, if discharge sensor 50 associated with the defibrillator station 22 detects that the defibrillator has been discharged, the associated communications circuitry, e.g., communication circuitry 52c, will initiate and transmit an alarm signal to remote central station 12 indicating discharge of a particular defibrillator.

Remote central station 12 is configured to identify a received signal with respect to a particular emergency equipment station. In this regard, the various signals transmitted by the emergency equipment stations (e.g., object detection signals, out-of-range pressure signals, etc.) include an identification code (e.g., an Internet Protocol address) or other information uniquely identifying the transmitting emergency equipment station. Installed location database 56 includes data for correlating the type of emergency equipment station (e.g., fire extinguisher station, defibrillator station, etc.) and the location of each station (e.g., room 407 on the fourth floor) with each station identification code. In other implementations, each emergency equipment station is configured to transmit signals to the remote central station via a radio frequency (RF) signal with a unique frequency, thereby allowing the remote central station to identify the source of the signal by the frequency of the received signal.

In other implementations, communications circuitry associated with emergency equipment station is configured for two-way communication between remote central station 12 and the respective station. In this implementation, the communication circuitry associated with each emergency equipment station is configured to receive requests for data from the remote central station. For example, the remote central station may request one or more emergency equipment stations to transmit the status of monitored internal and/or external conditions (e.g., object detected, current ambient air temperature, status of pressure of fluid in a fire extinguisher tank, etc.). In this implementation, the detection of objects (and their corresponding identities) may not be continuously transmitted to the remote central stations, but may only be transmitted when data is requested by the remote central station. In one particular implementation, data (e.g., detected objects, ambient air temperature data, alarm signals indicating occurrence of a sensed condition, etc.) is communicated via a network connection (e.g., a wireless or hardwire Ethernet connection) established between remote central station 12 and each respective emergency equipment station in the network of emergency equipment stations.

Figure 3:
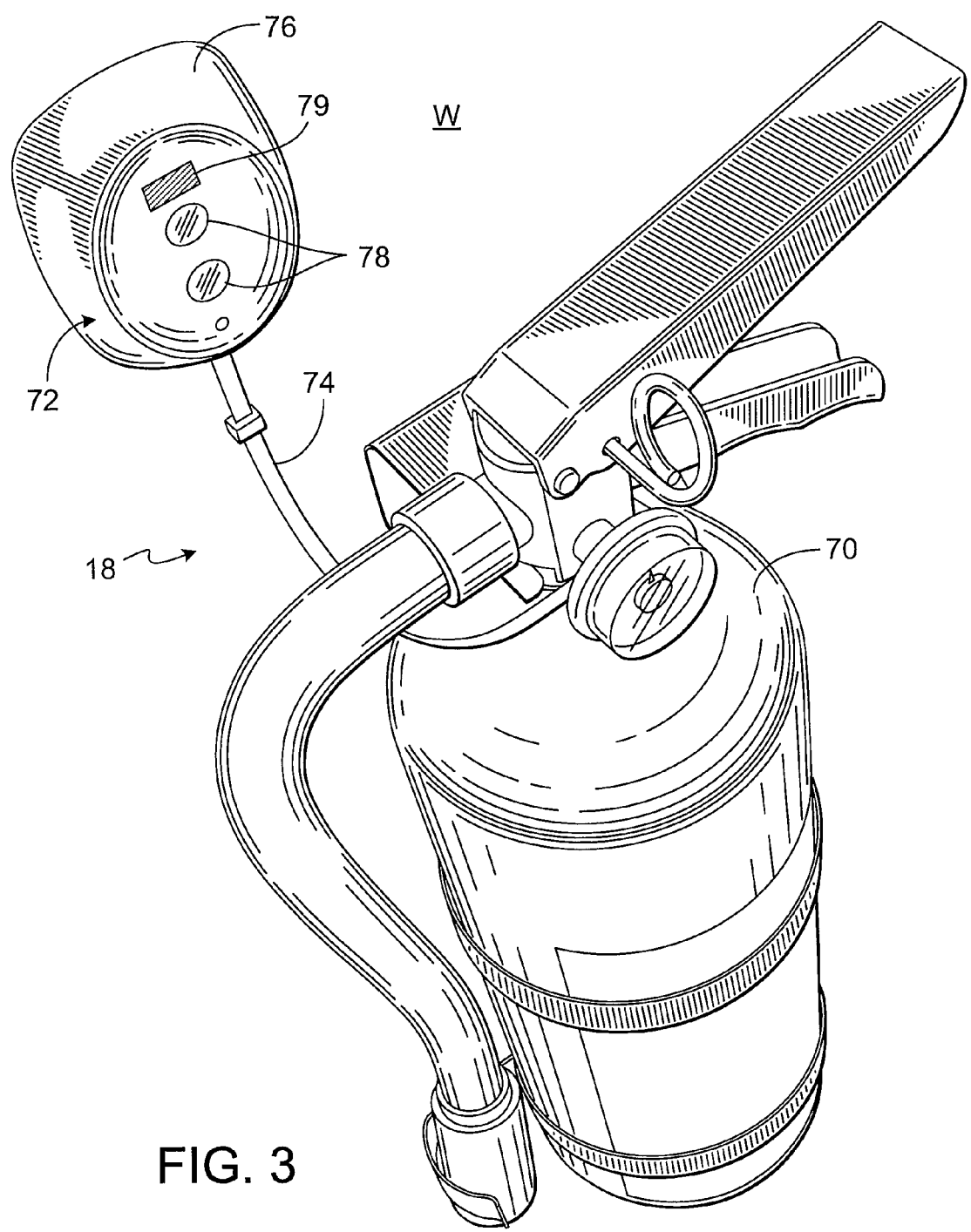
FIGS. 3-5 are perspective views of a fire extinguisher station.
Figure 4:
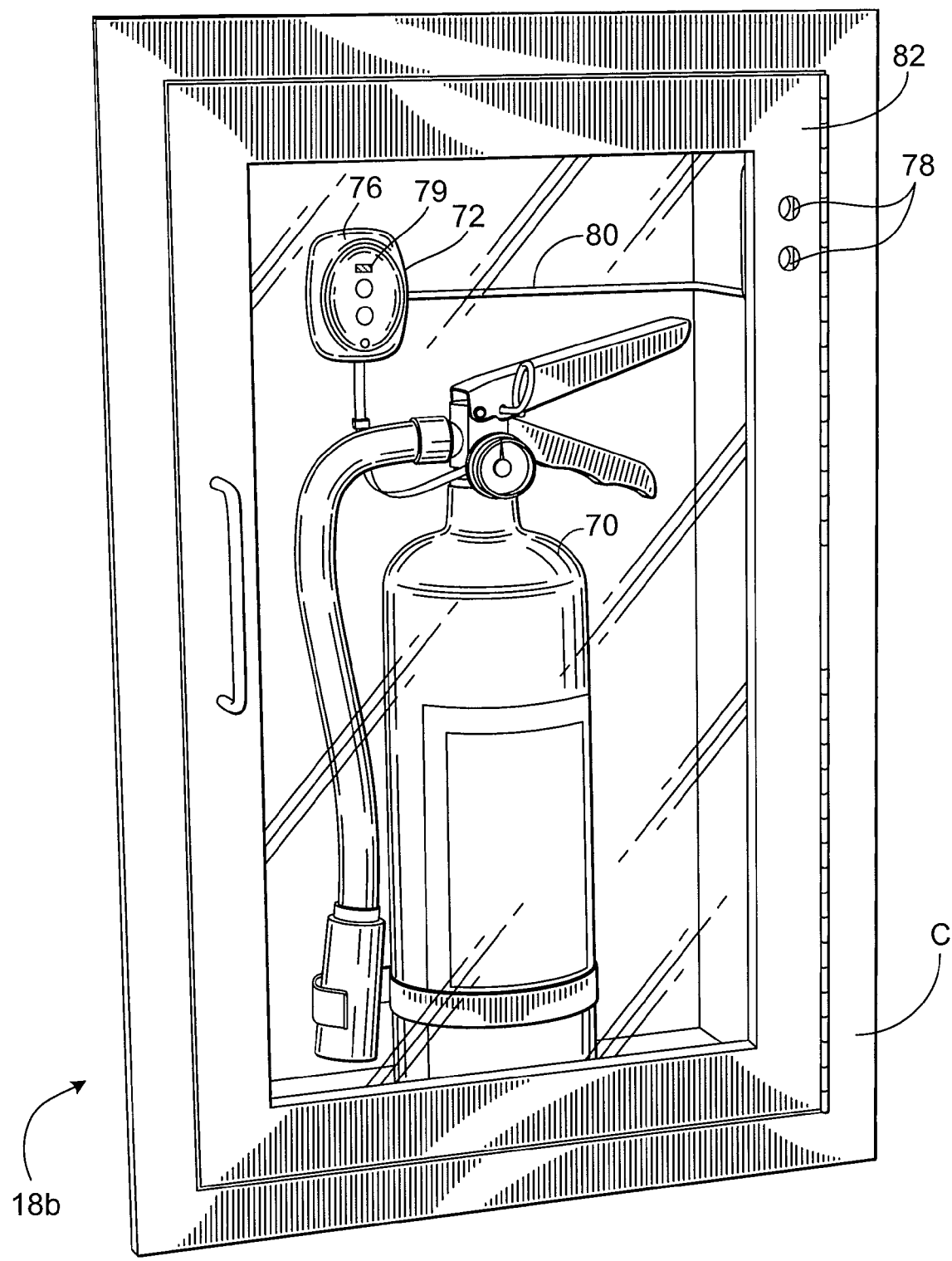

As an example of an emergency equipment station, a fire extinguisher station 18 shown in FIG. 3 includes a portable fire extinguisher 70 mounted to a wall, post, or other support surface, W, and in FIG. 4, another portable fire extinguisher station 18b includes an extinguisher 70 mounted within a wall box or cabinet, C. In these implementations, the fire extinguisher 70 at each fire extinguisher station 18, 18b is releasably connected to a docking station 72 by an electronics and communications tether 74 to provide releasable engagement for electronics and/or communications connection between docking station 72 and portable fire extinguisher(s) 70 at each station 18a, 18b. Typically signals issued from or to fire extinguisher 70 are transmitted over the electronics and communication tether 74. For example, a signal, initiated by one or more Hall Effect sensors included in fire extinguisher 70, which is indicative of out-of-range (low or high) pressure of the fire extinguishing material contained within the tank volume, is transmitted from fire extinguisher 70 across tether 74 to docking station 72 and then to remote central station 12 (shown in FIGS. 1-2).

In the implementation shown in FIG. 3, docking station 72 is fixedly mounted to the wall, W, at a predetermined position spaced generally above fire extinguisher 70. Docking station 72 consists of housing 76 containing sonic sensor 44 (shown in FIG. 2) and defining spaced apertures or windows 78 through which the sonic sensor emits and receives ultrasonic signals. In the implementation of FIG. 4, where docking station 72 is disposed with a wall cabinet, C, the sonic sensor is connected, e.g., by cable 80, to apertures or windows in the outer surface of cabinet door 82 for emitting and receiving the ultrasonic signals.

In the implementations shown in FIG. 3 and FIG. 4, the docking station 72 contains a tracking sensor (not shown) that senses objects through an aperture or window 79. In some arrangements the electromagnetic waves are emitted and collected by the tracking sensor via the window 79. For example, an electromagnetic signal issued from an RFID transceiver may be transmitted via an antenna through the window 79. A corresponding signal may be received from an RFID tag attached to an object (that provides an identification of the object). Additional windows and tracking sensors may also be included in the docking station housing 76. Furthermore, apertures and windows of the housing 76 may provide multiple functions. For example, the windows used be sensors for obstructions detection may also be used by one or more tracking sensors for collecting signal for object identification.

Various other types of sensors may also populate the docking station housing 72. For example, a temperature sensor that senses the ambient air temperature and communications circuitry for transmitting signals to remote central station 12 may be included in the housing.

Extending generally from the base of docking station housing 72 is electronics and communications tether 74 received by a connector in communication with a valve monitoring internal content pressure of the fire extinguisher. The length of tether 74, and the tenacity of engagement of the connection between the connector and the tether, are preferably selected so that any significant movement of fire extinguisher 70 relative to its installed position, i.e., the position in which it is placed at installation by a fire extinguisher professional, whether removal, or, in a preferred implementation, merely upon rotation with movement in excess of a predetermined threshold value, will result in dislodgement of tether 74 from the connector, initiating a signal to remote central station 12, as discussed above.

Docking station 76 may be powered by alternating current, e.g., by a hardwire connection into a facility's electrical supply, or it may be powered by direct current, e.g., by a battery within docking station housing 76. If powered by alternating current, an auxiliary power supply, e.g., in the form of a battery, may be provided in case of power outage.

Figure 5:
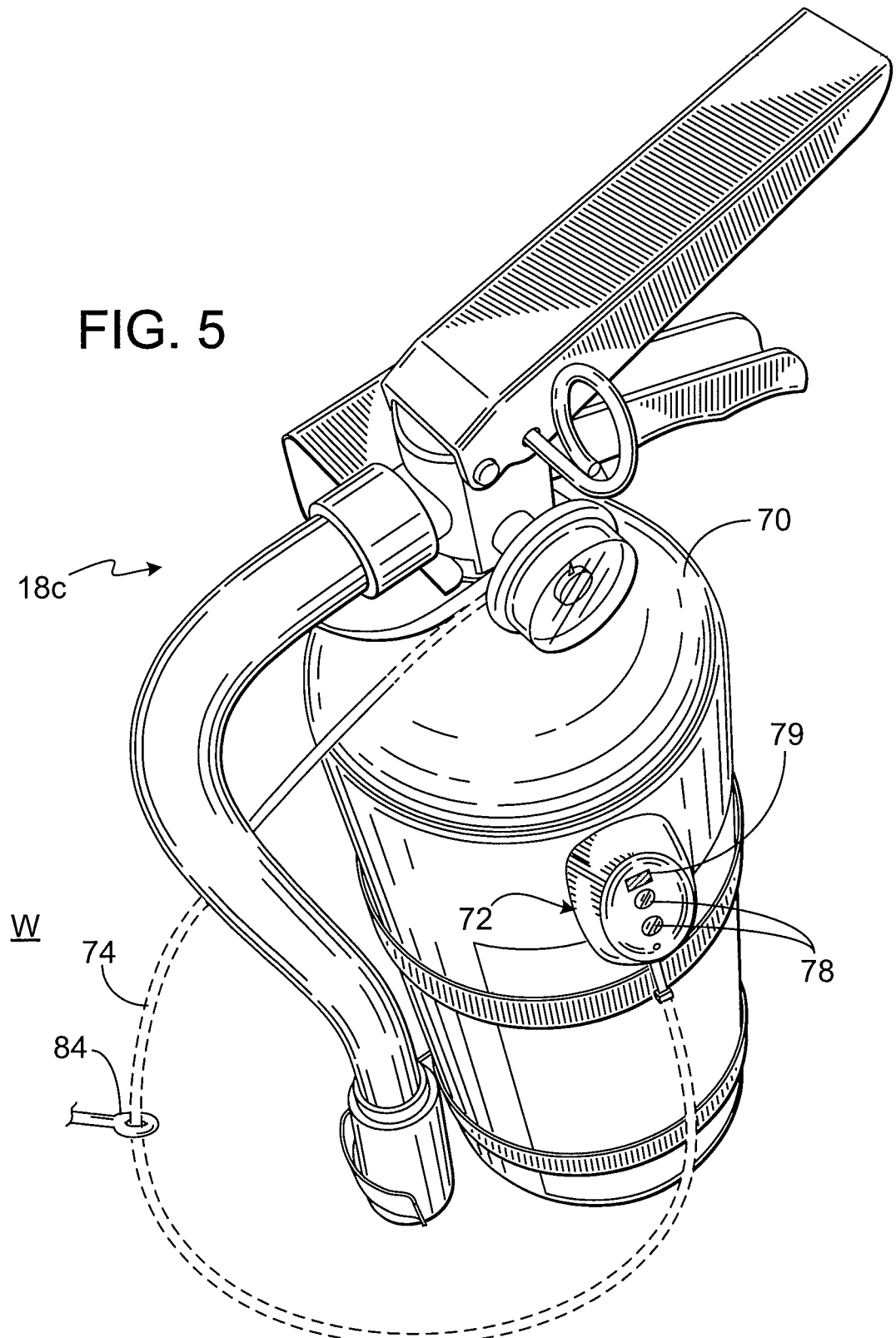

Referring to FIG. 5, in another implementation of portable fire extinguisher station 18c, components of docking station 72, as described above, may instead be mounted to fire extinguisher 70, e.g., within housing 76, thereby allowing the fire extinguisher to be located, if desired, without wall mounting or enclosure. In the implementation shown, housing 76 contains a tracking sensor 42 and sonic sensor 44 (both shown in FIG. 2). Housing 76 also defines apertures or windows 78 for detecting obstructions as previously mentioned and aperture 79 for use by the tracking sensor 42. Communications circuitry 52 is also disposed within housing 76, for communication of signals, e.g., wireless signals, between fire extinguisher station 18c and remote central station 12.

An electronics and communication tether 74 may extend between connections to housing 76 and fire extinguisher 70, as indicated in dashed line, e.g., engaged through an aperture of I-bolt 84 anchored into a wall W, such that any significant movement of fire extinguisher 70 relative to its position at rest, in excess of a predetermined threshold value, results in disengagement of the tether 74 from connection with extinguisher 70, thereby to initiate a wireless signal to remote central station 12. In another implementation (not shown), a tether or leash, e.g. in the form of a cord, wire, rope or the like, may extend from a first end secured, e.g., to a wall, to engagement of its second end in a socket defined, e.g., by housing 76, whereby dislodgement of the tether or leash from the socket initiates a wireless signal.

Communication circuitry 52 (shown in FIG. 2) is located within housing 74 to communicate by, for example, wireless signal between fire extinguisher station 18 and remote central station 12. Signals indicating the detection of an object are continuously communicated between remote central station 12 and fire extinguisher station 18. Additionally, upon detection of a monitored internal or external condition such as an out-of-range pressure condition, removal of an extinguisher from its installed position, or detection of an obstruction in front of station 18, a signal indicating the occurrence of the condition is transmitted (e.g., via a wireless or hardwire transmission) to remote central station 12. In this manner, a system of emergency equipment stations (e.g., fire extinguisher stations), distributed over a considerable area, are maintained in communication with remote central station 12.

Figure 6:
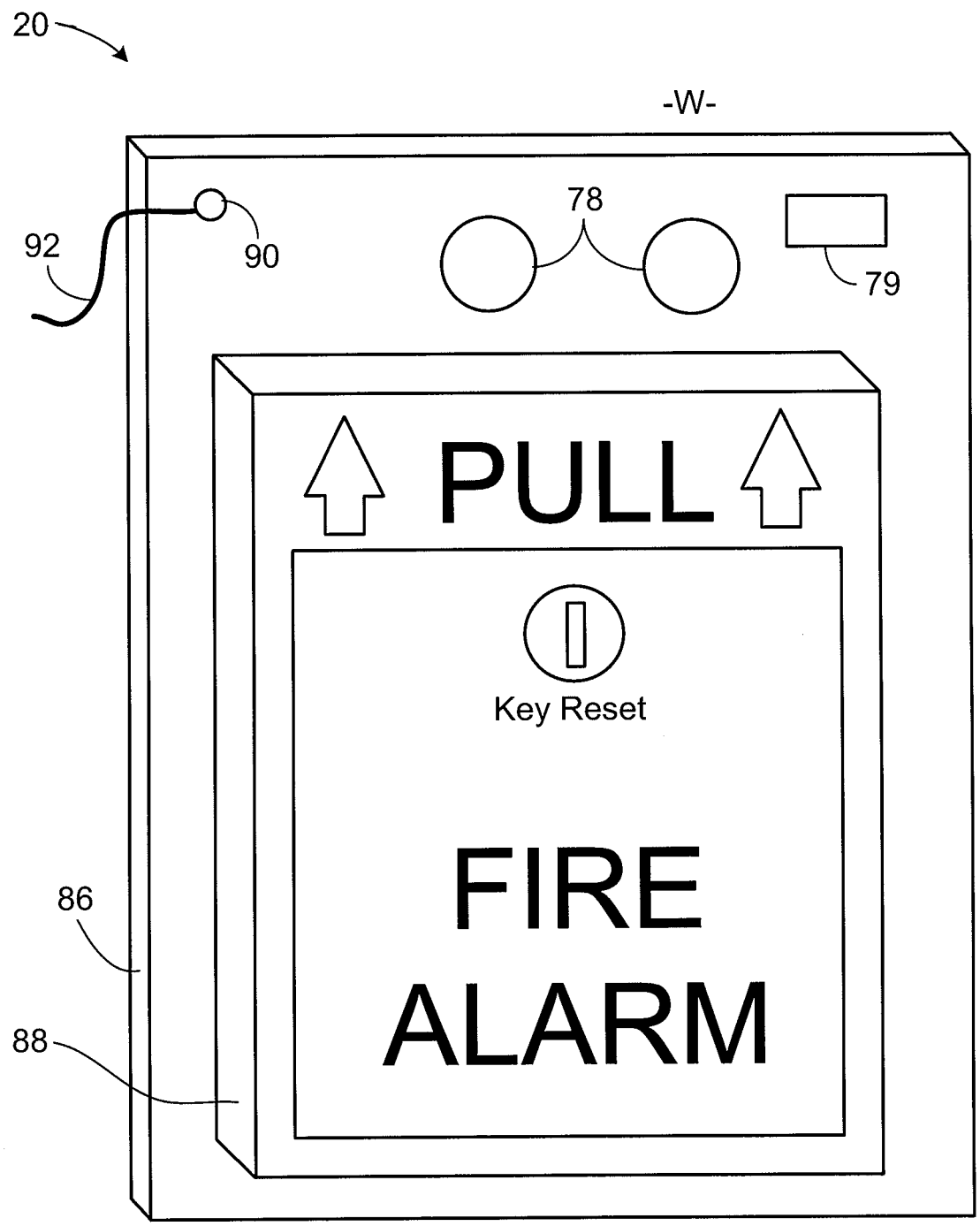
FIGS. 6-7 are perspective views of fire alarm pull stations.

Referring to FIG. 6, in another emergency equipment station, namely fire alarm pull station 22, components of docking station 72, as described above, are included in housing 86 that is shown mounted to a wall, post, or other support surface, W, and receives pull alarm 88. In the implementation shown, housing 86 contains tracking sensor 42, sonic sensor 44, and communications circuitry 52 (all shown in FIG. 2). Housing 86 also defines apertures or windows 78 for emitting and receiving ultrasonic signals to detect one or more objects that obstruct viewing of and access to fire alarm pull station 20. Also, aperture 79 is included in the housing for use by the tracking sensor. As mentioned, two or more windows or apertures may be included in the housing 86 for use by one or more tracking sensors. Additionally, if pull alarm 88 is pulled by a passerby in the event of an emergency to sound a fire alarm, a signal is issued by pull station 20 and transmitted to remote central station 12. In other implementations, fire alarm pull station 20 may initiate other signals based on other internal conditions associated within the pull station. For example, a signal may be initiated if a battery included in fire alarm pull station 20 needs to be replaced or recharged.

The tracking sensor transmits a signal to remote central station 12 indicating the detection of an object in the vicinity of the fire alarm pull station 20 (for object identification). In some implementations, signals indicative of an object detection (or not) may be continuously sent, periodically sent, or sent upon the detection of the object, or by using a similar methodology or technique. Additionally, the sonic sensor initiates a signal to indicate an obstruction that may be restricting visibility of or access to fire alarm pull station 20. To initiate these signals, communications circuitry 52 is also disposed within housing 86 for transmitting signals to remote central station 12. To transmit a signal, communications circuitry 52 sends the signal via a hardwire connection or a wireless link from housing 86 to remote central station 12. To provide a hardwire connection, in this implementation, housing 86 includes connection terminal 90 for connecting to hardwire connection 92 for transmitting signals to and receiving signals from remote central station 12. In other implementations a wireless link is established between housing 86 and remote central station 12 for transmitting and receiving signals. For example, communication circuitry 52 included within housing 86 may include an RF transmitter and antenna for transmission of RF signals to remote central station 12. Also, in some implementations communication circuitry 52 is capable of receiving wireless signals from remote central station 12, other wireless devices (e.g. cellular telephone, etc.), or from one or more other emergency equipment stations for relaying signals in a networking scheme. By forming a network (e.g., a local area network, wide area network, or similar) with hardwire connections or wireless links, or a combination of hardwire connections and wireless links, a system of emergency equipment stations, distributed over a considerable area, is capable of being remotely monitored by remote central station 12. Additionally, in some implementations, housing 86 includes communications circuitry 52 configured to transmit signals via a hardwire connection and a wireless link, thus providing redundant transmission pathways between remote central station 12 and housing 86. Some or all of the information received by remote central station 12 may be forwarded to emergency response personnel to assist in responding to an emergency situation.

Along with transmitting internal conditions (e.g., battery replacement or recharging, etc.) and external conditions (e.g., object detection and identification, ambient air temperature, detection of an obstruction, etc.) associated with fire alarm pull station 20, in some implementations housing 86 of the fire alarm pull station also provides local indications that the pull station has been operated, e.g., in the event of an emergency. For example, housing 86 can include or be in communication with an audible signaling device (e.g., a speaker) for emitting an audible tone or signal (e.g., verbal commands) to alert people in the local vicinity to a detected obstruction of the pull station or other external condition such as the operation of the pull station by a passerby due to fire. The audible signal may also consist of a recorded information message, e.g., instructions for evacuation or for assisting personnel located near fire alarm pull station 20. Also, housing 86 may include one or more alert lights, strobes, or other similar lighting devices that are driven by circuitry included in housing 86 such that the alert lights illuminate, flash, or strobe for visually alerting personnel in the vicinity that access to and view of fire alarm pull station 20 is obstructed, or that pull station 20 has been actuated.

Figure 7:
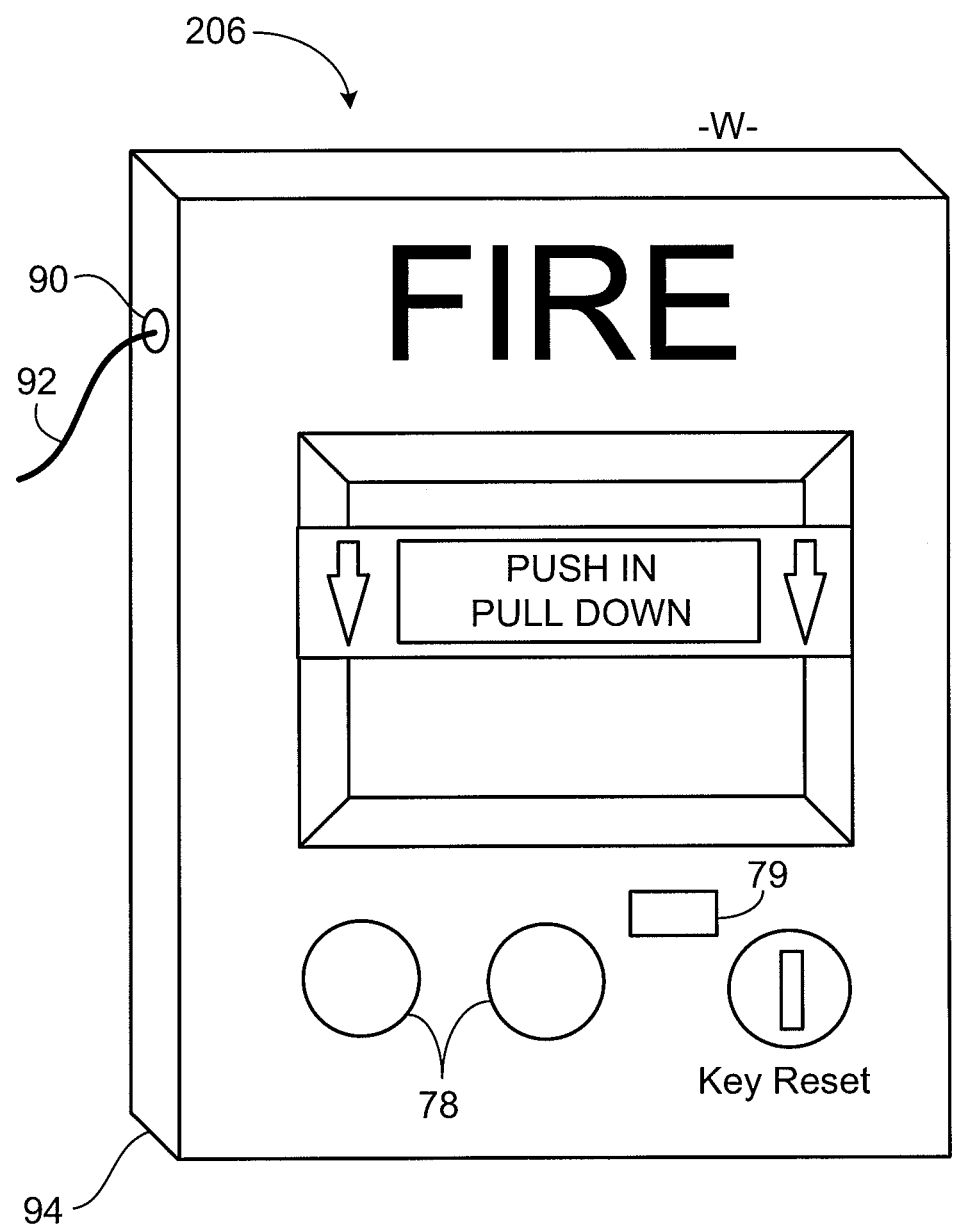

Referring to FIG. 7, in another implementation of fire alarm pull station 20b, components of docking station 72, as described above, are included within the housing of pull alarm 94, rather than in a separate housing that receives the pull alarm as shown in FIG. 6. In the implementation of FIG. 7, fire alarm pull station 20b includes communications circuitry 52, temperature sensor 42, sonic sensor 44 (all shown in FIG. 2) and defines the apertures or windows 78 for emitting and receiving ultrasonic signals for detecting obstructions at ranges, e.g., from about 6 inches to about 10 feet dependent, upon the environment. Including the tracking sensor and sonic sensor (and possibly other sensors such as a temperature sensor), along with communication circuitry 52 within fire alarm pull station 20b, permits pull station 20b of being located on a wall, post, or other support surface, W, in a relatively smaller area that might otherwise be ill-suited for supporting the relatively larger housing 86 shown in FIG. 6.

Additionally, by including the tracking sensor within the fire alarm pull station (and aperture 79), a signal can be transmitted (e.g., continuously, periodically, upon occurrence of a trigger, etc.) to remote central station 12 to indicate object detection (and identification) in the vicinity of the fire alarm pull station. Similarly, by including the sonic sensor in a fire alarm pull station, along with apertures or windows 92, obstructions to visibility and accessibility of the pull station can be detected by the sonar module for issue of a signal is issued by electronic and communication circuitry 94 to remote central station 12. Also, similar to housing 86, in this implementation, fire alarm pull station 94 includes connection terminal 90 for connecting hardwire connection 92 to the pull station for transmitting signals to remote central station 12. Alternatively, or in concert with hardwire connection 92, communications circuitry 52 (shown in FIG. 2) within fire alarm pull station 94 may include a wireless transmitter and/or a transreceiver and antenna for transmitting and/or receiving wireless signals to/from remote central station 12 and provide capability for distribution of a system of fire alarm pull stations over a considerable area while maintaining wireless communication between each fire alarm pull station and remote central station 12. Additionally, in some implementations, fire alarm pull station 94 includes an audible signaling device (e.g., a speaker) and/or alert lights for issuing an alert to nearby personnel or passersby that the pull station is, e.g., being obstructed.

Figure 8:
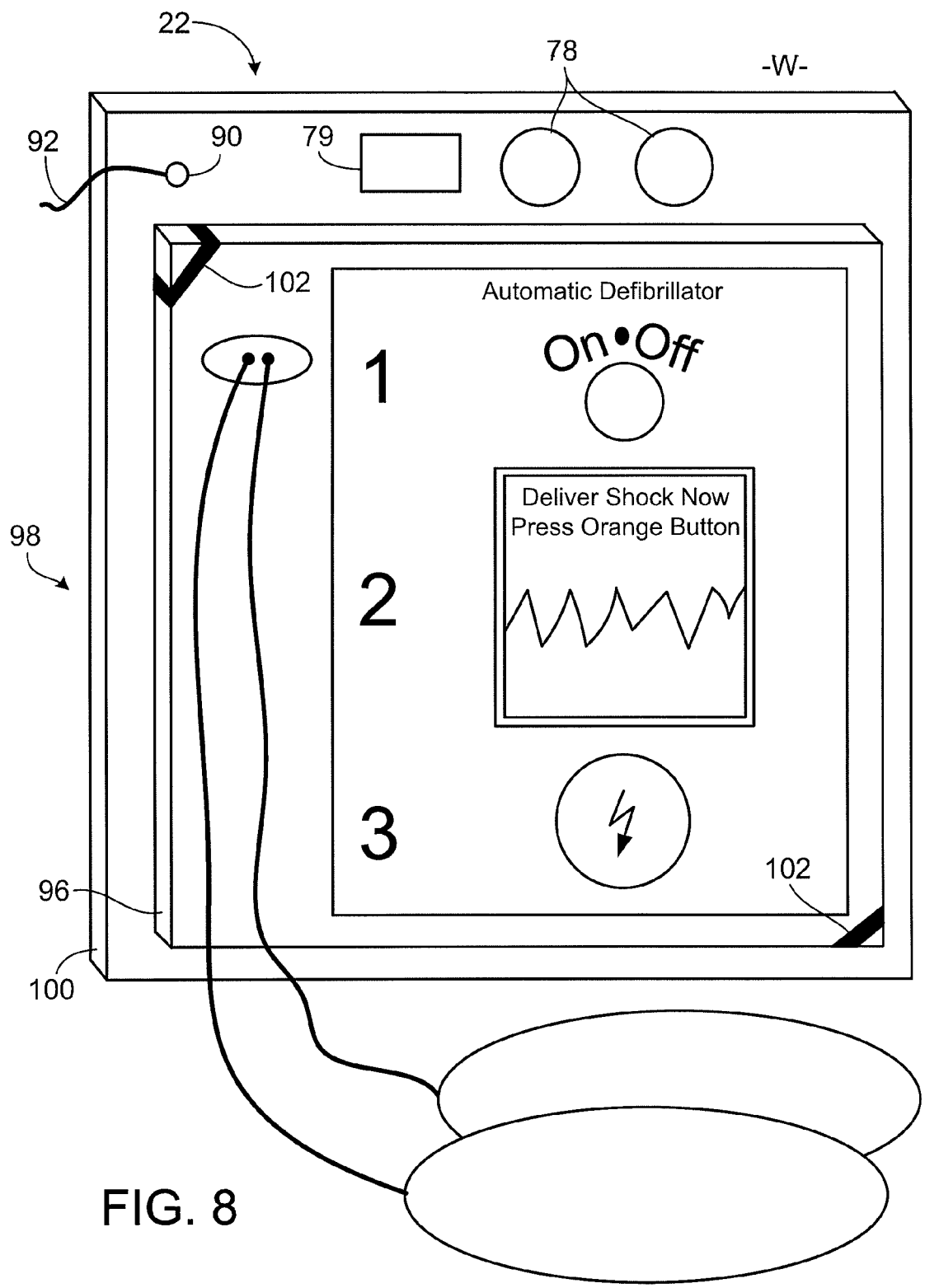
FIG. 8 is a perspective view of a defibrillator station.

Referring to FIG. 8, another emergency equipment station, namely defibrillator station 22, includes defibrillator 96 attached to docking station 98 by one or more mechanical fasteners 102 (e.g., a clips, fastening material, etc.). Typically, defibrillator station 22 is mounted to a wall, post, or other support surface, W, so that defibrillator 96 is accessible by trained personnel or the general public for use during an emergency, e.g., such as a person suffering from sudden cardiac arrest or other life-threatening aliment. By distributing a system of defibrillator stations, for example, throughout an airport, shopping center, or other facility accessible by the public, in the event of an emergency, a defibrillator can be removed from a relatively nearby defibrillator station to provide assistance.

Docking station 98 includes housing 100 containing tracking sensor 42 (shown in FIG. 2) (and aperture 79) for sensing (and identifying) objects near the defibrillator station, sonic sensor 44 and apertures or windows 78 for detecting the presence of an obstruction restricting access to the defibrillator, discharge sensor 50 for detecting when defibrillator 96 has delivered a shock, and communication circuitry 52c (shown in FIG. 2) for transmitting signals indicating various monitored internal and external conditions.

Similar to the fire extinguisher stations, e.g., station 18 shown in FIG. 3, communications circuitry 52c transmits (e.g., continuously, periodically, upon occurrence of a trigger, etc.) to remote central station 12 a signal indicating detection (for identification) of one or more objects near defibrillator station 22. Additionally, upon detection of an obstruction by the sonic sensor or detection that the defibrillator has been discharged by the discharge sensor, communications circuitry 52c initiates and transmits a signal to remote central station 12, which identifies the defibrillator station and the sensed condition (e.g., detected object, presence of an obstruction, defibrillator discharge, etc.). Signals indicating monitored predetermined internal and external conditions are transmitted in this implementation to remote central station 12 via hardwire connection 92 connected to terminal 90. However, in other implementations, signals may be transmitted via a wireless link in lieu of or in addition to a hardwire connection.

Additionally, in some implementations, other internal and/or external conditions may be sensed by defibrillator station 22 and communicated to remote central station 12. For example, if the defibrillator is removed from the docking station (e.g., in the event of an emergency), or if an internal battery needs attention (e.g., replacing, recharging, etc.), a signal is transmitted to the remote central station over the hardwire connection and/or in a wireless signal from an antenna.

Along with providing a signal to remote central station 12 indicating internal and/or external conditions of defibrillator 92 and/or defibrillator station 22, in some implementations the defibrillator station includes an audible signaling device (e.g., a speaker) that issues an audible tone, signal, or message for alerting personnel and/or the general public to one or more of predetermined internal and external conditions. For example, if defibrillator station 92 is obstructed, or if defibrillator 92 is removed from the defibrillator station, an audible tone may be emitted by the audible signaling device. Also, defibrillator station 22 may include one or more alert lights, strobes, or other similar lighting devices for similarly alerting personnel and/or the general public to the one or more of the predetermined internal or external conditions associated with the defibrillator station or defibrillator 92.

Figure 9:
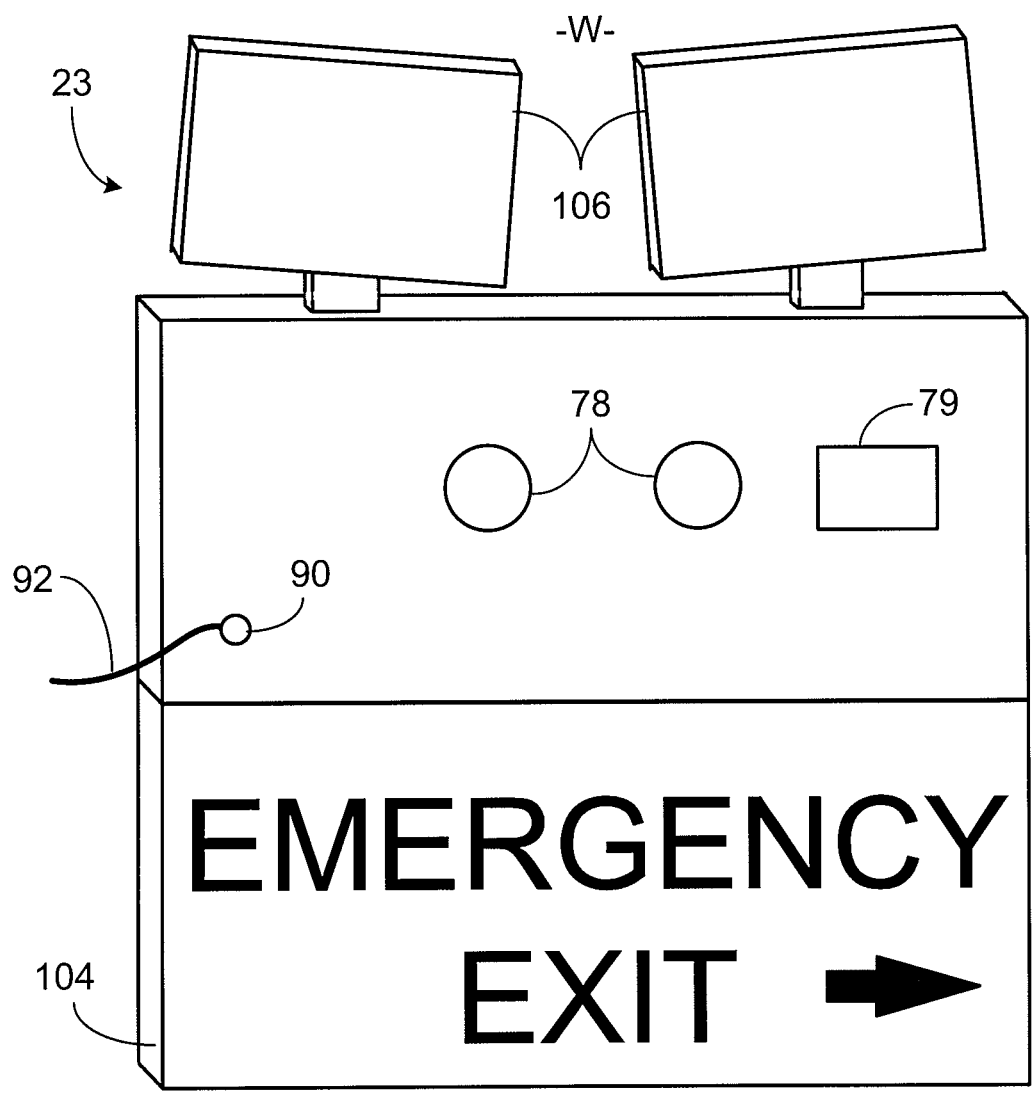
FIG. 9 is a perspective view of an emergency lighting station.

Referring to FIG. 9, another emergency equipment station, namely an emergency lighting station 23, includes housing 104 and a pair of emergency lights 106 that provide illumination in the event of an emergency (e.g., a fire, a power outage, etc.). In some implementations, activation of emergency lights 106 is controlled remotely, e.g., from remote central station 12, or controlled locally by circuitry and sensors (e.g., a smoke detector) included in housing 104 or positioned in a nearby location (e.g., mounted in a ceiling). Typically, emergency lighting station 23 is mounted to a wall, post, or other support surface (e.g., a ceiling, doorway, etc.), W, for illuminating the local area during an emergency. In some implementations, a system of emergency lighting stations is distributed throughout a commercial, industrial, educational, or other similar type of facility to provide emergency lighting. Additionally, in this implementation, emergency lighting station 23 includes an "EMERGENCY EXIT" signal, which may or may not illuminate while directing people to an appropriate egress point (e.g., doorway) during an emergency.

Similar to previously mentioned implementations, housing 104 of emergency lighting station 23 contains (at least one) tracking sensor 42 (and aperture 79) for detecting (and identifying) one or more objects near the emergency lighting station.

Housing 104 also includes sonic sensor 44 (shown in FIG. 2) and apertures or windows 78 for detecting obstructions. By including the sonic sensor within emergency lighting station 23, obstructions to operation of the emergency lighting station, i.e., illumination of the area intended to be illuminated, are detectable by the sonar module and a signal is initiated from communications circuitry 52 also included in the station. Similar to previously mentioned implementations, emergency lighting station 23 includes connection terminal 90 that connects to hardwire connection 92 for transmitting signals to remote central station 12. In some implementations the emergency lighting station includes wireless communication circuitry and an antenna in lieu of or in addition to a hardwire connection for providing wireless transmission of the signal to remote central station 12. Additionally, in some implementations, the communication circuitry includes circuitry for transmitting both wireless signals over an antenna and hardwire signals via the hardwire connection for redundancy to provide a back-up signal transmission pathway.

As in other emergency equipment stations described above, communications circuitry 52 (shown in FIG. 2) is configured to continuously transmit a signal indicating the ambient air temperature to remote central station 12. In addition, communications circuitry 52 is configured to initiate a signal sent from emergency lighting station 24 to remote central station 12 upon the detection of one or more of the predetermined external conditions associated with the station, such as an obstruction detected by the sonar module through apertures or windows 78. In other implementations, the communications circuitry may be configured to initiate a signal to remote central station 12 upon detection of a predetermined internal conditions associated with station 23 such as a battery back-up needing replacement or recharging, or an emergency lights 106 needing replacement. Additionally, emergency lighting station 23 may include an audible signaling device (e.g., a speaker) for emitting an audible tone, signal, or message to alert facility personnel and/or the general public in the vicinity that the station is currently obstructed or that another predetermined internal or external condition has occurred. Also, emergency lighting station 23 may include one or more alert lights, strobes, or other similar lighting devices, in addition to emergency lights 106, for emitting a visual alert to indicate, e.g., that the emergency lighting station is obstructed.

Figure 10:
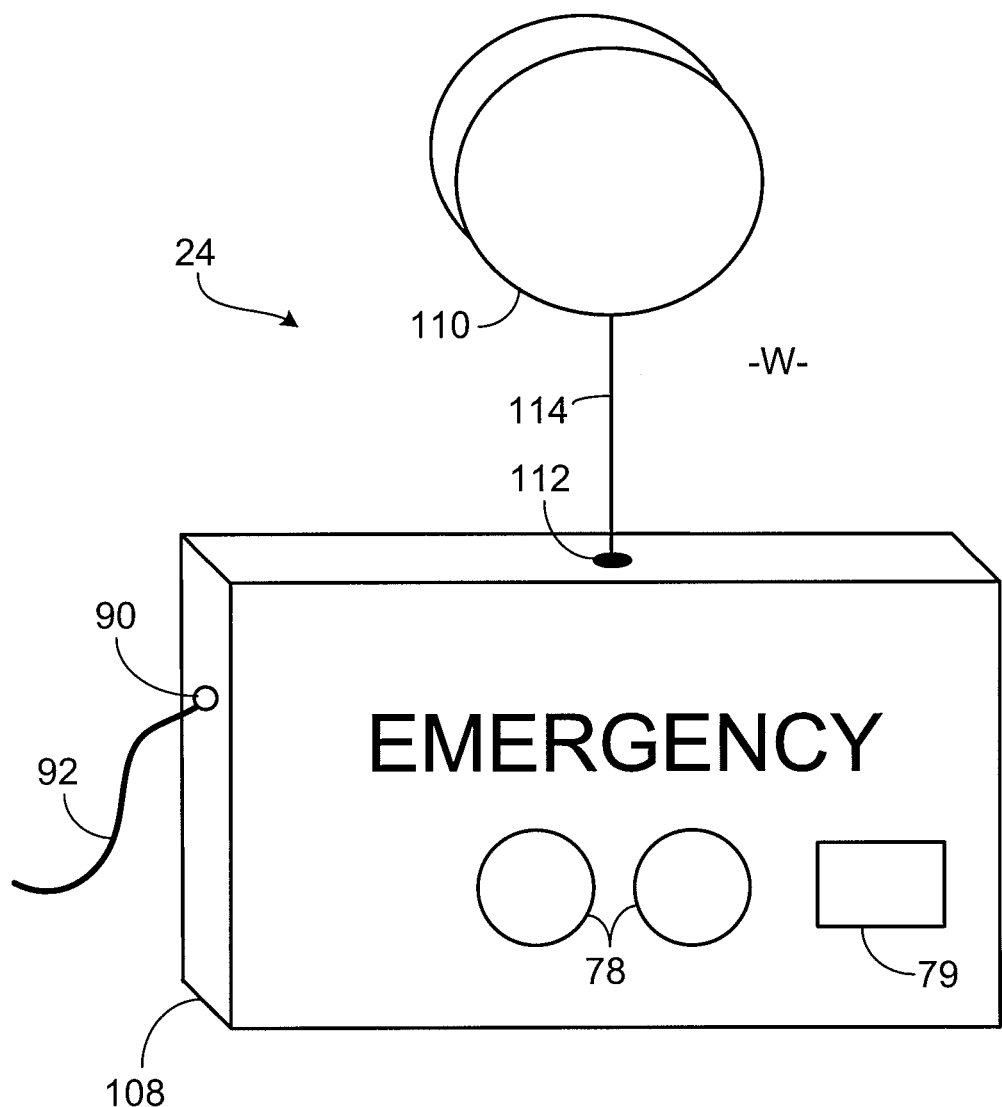
FIG. 10 is a perspective view of an emergency egress station.

Referring to FIG. 10, in another emergency equipment station, namely emergency egress station 24, includes housing 108 that is in communication with, e.g., strobe 110 providing illumination in the event of an emergency (e.g., a fire, a power outage, etc.). In some implementations, activation of strobe 110 is controlled remotely, e.g., from remote central station 12, or controlled locally by circuitry and sensors (e.g., a smoke detector) included in emergency egress station 24 or positioned in a nearby location (e.g., mounted in a ceiling). Typically, emergency egress station 24 is mounted to a wall, post, or other support surface (e.g., a ceiling, doorway, etc.), W, for illuminating the local area during an emergency. Furthermore, in some implementations, emergency egress station 24 is mounted on the support surface approximately slightly above floor level, such that a person crawling along the floor in the event of an emergency (e.g., fire) can detect the illuminating strobe for directing to an appropriate egress point, such as an emergency exit doorway.

Similar to previously mentioned implementations, housing 108 of emergency egress station 24 contains tracking sensor module 42 (shown in FIG. 2) (and aperture 79) for detecting (and identifying) one or more objects near the station. Housing 108 also contains sonar module 44 and defines apertures or windows 78 for detecting obstructions. By including sonar module 44 within housing 108, obstructions to operation of emergency egress station 24, e.g., an emergency exit way (door, window, etc.) associated with the emergency egress station, are detectable by the sonar module and a signal is initiated from communications circuitry 52 also included in the housing. Similar to previously mentioned implementations, emergency egress station 24 includes connection terminal 90 that connects to hardwire connection 92 for transmitting signals to remote central station 12. In some implementations, the emergency egress station includes wireless communication circuitry and an antenna in lieu of or in addition to a hardwire connection to provide wireless transmission of the signal to remote central station 12.

As in other emergency equipment stations described above, communications circuitry 52 is configured to continuously transmit a signal indicating ambient air temperature near the emergency egress station to the remote central station 12. In addition, communications circuitry 52 is configured to initiate a signal sent from emergency egress station 24 to remote central station 12 upon the detection of one or more of the predetermined external conditions associated with the station, such as an obstruction detected by the sonar module through apertures or windows 78. In other implementations, the communications circuitry may be configured to initiate a signal to remote central station 12 upon detection of predetermined internal conditions associated with the station 24, such as a battery needing replacement or recharging, or a strobe light needing replacement. Additionally, emergency egress station 24 may include an audible signaling device (e.g., a speaker) for emitting an audible tone, signal, or message to alert facility personnel and/or the general public in the vicinity that the station is currently obstructed or that another predetermined internal or external condition has occurred. Also, emergency egress station 24 may include one or more additional strobes, or other similar lighting devices, for emitting a visual alert to indicate, e.g., that emergency egress station 24 is obstructed or in the event of an emergency, as communicated by a signal received via hardwire connection 92 or an antenna.

In this particular implementation housing 108 includes terminal 112 that connecting wire 114 between housing 108 and strobe 110 so that the strobe is activated by a signal from the housing. Alternatively, an antenna (which may be either external to the housing or included within in the housing) can establish a wireless link between the housing and the strobe 110 such that a wireless signal transmitted from the housing activates the strobe. Also, in some implementations, strobe 110 is activated by a signal initiated by another signal received by housing 108. For example, in some implementations, housing 108 is in communication with emergency equipment such as a fire alarm pull station, defibrillator, smoke detector, or other emergency equipment providing a signal to activate strobe 110 in the event of an emergency.

Similar to docking station 76 (shown in FIG. 3), in some implementations, housing 108 is fixedly mounted to the wall, W, with or without strobe 110, at a predetermined position spaced from a fire extinguisher, fire alarm pull station, defibrillator, or other piece of emergency equipment. So, for example, rather than incorporating the components of docking station (e.g., temperature sensor 42, sonic sensor 44, apertures 78, communications circuitry 52, etc.) into a housing positioned in close proximity to the emergency equipment, or incorporated into the emergency equipment, the components are incorporated into housing 108 that is positioned a distance away from the equipment and in communication with the emergency equipment via hardwire connection 92 or by wireless link established with an antenna. By communicating with the emergency equipment in the event of an emergency (e.g., a fire alarm pull station is pulled), a signal is sent from the emergency equipment to housing 108 to activate strobe 110 or, for example, in response to receiving the signal, the housing sends a signal over hardwire connection 92 to remote central station 12, or both.

Referring now to FIG. 11, a flowchart 200 represents a particular arrangement of operations for communicating information in the system 10. Typically the operations are carried out on computing devices of the system 10 including computing devices of the remote central station 12. In some implementations, the operations may be executed in processors present in these devices.

Operations may include sensing 210 or collecting data on an object or parameter internal or external to the emergency equipment station. In one implementation, sensing may include detecting the presence or absence of an object by a sensor. For example, the sensor may detect the absence of an emergency assistance device such as a fire extinguisher or a defibrillator. The sensor may also detect an obstruction obstructing access to any part of the emergency equipment station. The objects sensed by the sensor may include any animate or inanimate object. An emergency personnel such as a fireman or a policeman could be an example of an animate object. Animate objects could also include a person or animal requiring attention or help. Inanimate objects may include, without limitation, any device, equipment or obstruction to accessing the emergency equipment station. In some implementations, the sensed object could be a combination of animate and inanimate objects. An example of such a combination is a tag or identification worn or attached to a person or animal. In such examples, the sensing may include mutual coupling between a sensor and the tag or identification module of the object. In some implementations, sensing may include tracking one or more objects. Tracking an object may involve detecting a presence of an object as well as identifying the object. Tracking may also include communicating to the central station updates on the location of the object.

In some examples, sensing may include collecting data on one or more parameters related to conditions internal or external to the emergency equipment station. The conditions may be predetermined and selectable. In some implementations, collecting data may include quantitatively measuring one or more parameters or metrics. In other implementations, sensing may include detecting a presence or absence of a condition. For example, it may be desirable in some circumstances to detect whether a harmful gas is present at a location in order to determine whether emergency personnel may access the location. Such detection may also dictate necessary precautions for accessing the area. Parameters that may be sensed includes, without limitation, temperature, heat, pressure, light, sound, radiation, electric current, voltage, magnetic field, motion, orientation, distance, proximity, odor, humidity and a presence of a substance.

The operation of sensing may be executed using any type and kind of sensor. For example, the sensor used may be a thermal sensor such as a thermometer, thermocouple, calorimeter or heat-flux sensor. In other implementations, the sensor may be a mechanical sensor such as a barometer, gas meter, flow sensor, strain gauge, vibration and shock detector or hygrometer. In still other implementations, the sensor may be a chemical proportion sensor such as an oxygen sensor, pH sensor or carbon monoxide detector. The sensor could also be an electromagnetic sensor such as multimeter, ammeter, voltmeter or magnetometer. In some implementations, the sensor may include a radiation sensor such as a Geiger counter or an earthquake sensor such as a seismometer. It should be noted that the foregoing examples are mentioned for illustrative purposes only and should not be construed as limiting in any sense. Any combination of the above types and/or other types of sensors may be used without departing from the scope of the present application. There may be one or more sensors at the emergency equipment station.

Operations may include transmitting 220 the sensed data from the emergency equipment station to a remote central station. In some implementations, the data is transmitted by way of a network of emergency equipment stations. The network may include a plurality of emergency equipment stations or nodes connected in a mesh configuration. In some implementations, the plurality of emergency equipment stations may each have a receiver and a transmitter. The receiver may receive the data from a node in the network and the transmitter may transmit the data to a next node. In some implementations, the data may be updated while being transmitted over the network. For example, consider a situation where data on a last known location (say location A) of an object is being transmitted via an emergency equipment station in the network. Before relaying the data to a next node in the network, the station senses or receives data that the object has moved to another location B. In such a situation, the station may update the data on the location of the object before relaying it to the next node. In some implementations, a history of the last known locations may be transmitted in order to track a movement of the object.

The operations may further include transmitting 230, from the central station, information representing the data. The central station may communicate with a transmitter for sending the information. The transmission may be sent, without limitation, using any wired or wireless network and using any transmission algorithm as apparent to one skilled in the art. In some implementations, the emergency equipment stations may directly transmit at least some information without using the central station as an intermediary. In other implementations, the central station may cooperate or coordinate with one or more emergency equipment stations to facilitate the transmissions.

The transmitting operation may involve sending any form and nature of information. For example, the central station may transmit a temperature map of a building and/or a facility where the system described herein is deployed. The information may include tracking data related to a person or object. In some cases, a source and nature of emergency may be included in the information. For example, if a fire extinguisher is dislodged on a third floor of a building, this information may be transmitted to incoming fire personnel. In such a case, the fire personnel will know beforehand that a fire has probably broken out on the third floor. In some cases, auxiliary information may be derived from the information directly deduced from the data. For example, if an emergency equipment station detects the presence of a toxic gas, the auxiliary information that the emergency personnel must have gas masks may be transmitted to the personnel beforehand. The transmitting step may involve point to point transmission to a facility, building or vehicle depending on a type or nature of emergency. The transmitting may also be executed in a broadcast mode where a plurality of receivers can receive the transmission.

In some implementations, the data may be processed by the central station prior to transmitting. Such processing may include converting one form of data to another form. In some implementations at least a part of the processing may be executed at a facility, vehicle or device located remotely from the central station. In some cases, at least a part of the processing may be carried out at the emergency equipment station. In other cases, one or more entities or devices described herein may carry out the processing in communication with each other. The central station may coordinate with these one or more entities and device in carrying out the processing. In some cases, the processing may include simply forwarding the data to a receiver without performing any operation on it.

Processing may involve any mathematical, logical or graphical operation. Any software, hardware or a combination thereof may be used for the processing. The central computer may process data in communication with one or more databases. For example, the central computer may communicate with a database that stores locations of a plurality of emergency equipment stations. The database may also include a floor plan and/or map of a building and/or property where the system described herein is deployed. The database may also include an object tracking database. The processing step may output information based on at least the data received from a sensor. The step of processing may also include communicating with a plurality of emergency equipment stations to track a person or object moving inside a facility and/or building. For example, a facility may track how firemen and/or other emergency personnel are distributed and/or moving inside a building. The facility may also be able to track a location of a person, animal or object that needs help and issue instructions to a personnel accordingly.

A number of implementations of the invention have been described. Nevertheless, it will be understood that various modifications may be made without departing from the spirit and scope of the invention. For example, wireless signaling technology may incorporate telecommunication schemes (e.g., Bluetooth or similar) to provide point-to-point or multipoint communication connections among, e.g., fire extinguisher stations and/or other emergency equipment stations (e.g., a defibrillator station) and/or the remote central station. These telecommunication schemes may be achieved, for example, with local wireless technology, cellular technology, and/or satellite technology. The wireless signaling technology may further incorporate spread spectrum techniques (e.g., frequency hopping) to allow the emergency equipment stations to communicate in areas containing electromagnetic interference. The wireless signaling may also incorporate identification encoding along with encryption/decryption techniques and verification techniques to provide secure data transfers among the devices.

In other implementations, the emergency equipment stations (e.g., a defibrillator station) and/or remote central station may include or otherwise be associated with a Global Positioning System (GPS). GPS may be used to determine, for example, the geographic location of each emergency equipment station and provide location coordinates, via the wireless signaling technology, to the other emergency equipment stations (e.g., the defibrillator station) and/or the remote central station. Thus, the GPS system may provide the location of the fire alarm pull stations and allow, for example, tracking of the frequency that stations located in a particular region of a facility are obstructed.

Also, the signaling may use networking techniques to provide one-directional and/or multi-directional communications among the devices. In one example, signals from emergency equipment stations may be networked asynchronously, such as in an asynchronous transfer mode (ATM). The signals may also be networked synchronously, such as, for example, in a synchronous optical network (SONET). In still another example, the signals may be transmitted over a landline in an integrated services digital network (ISDN), as well as over other similar media, for example, in a broadband ISDN (BISDN).

A remote central station for transmitting sensory data to emergency response personnel may also be employed for remote inspection of multiple facilities, each including multiple or a system of emergency equipment stations. Communication between emergency equipment stations and a remote central station, including hard-wire and wireless communication, may be carried on directly, or indirectly, e.g. via relaying devices, including other emergency equipment stations.

Accordingly, other implementations are within the scope of the following claims.

What is claimed is:

1. A system for communicating information comprising:
    a network of emergency equipment stations including at least one emergency equipment station, the emergency equipment station comprising:
        an emergency assistance device,
        a first sensor configured to detect an object within a vicinity of the emergency equipment station and to sense a movement of the object, wherein the object comprises an inanimate object,
        a signaling device,
        communication circuitry, and
        a second sensor configured to sense at least one selectable predetermined internal condition;
    a system to determine a geographic location of the emergency equipment station including a number of location coordinates for the emergency equipment station;
    processing circuitry configured to receive data from the first sensor and to determine when the object obstructs access to the emergency assistance device;
    a central station remotely located from the emergency equipment station and configured to communicate with the communication circuitry of the emergency equipment station and the network of emergency equipment stations, the central station also configured to receive data from the first sensor and the second sensor, wherein the central station is further configured to track movement of the object inside a building; and
    at least one receiver and at least one transmitter, each remotely located from the central station, the receiver configured to receive information regarding a location of the object from at least one of the emergency equipment station and the central station, the receiver further configured to update the information based on sensed or received data, the transmitter configured to relay the updated information to at least one of the central station and another emergency equipment station.

2. The system of claim 1, wherein the at least one receiver is deployed in at least one of a building, a vehicle, and a hand-held device.

3. The system of claim 1, wherein the second sensor is configured to sense an ambient temperature.

4. The system of claim 1, wherein the emergency assistance device comprises at least one of a fire extinguisher, a fire pull alarm, an emergency lighting device and a defibrillator.

5. The system of claim 1, wherein the network of emergency equipment stations includes a mesh network configuration.

6. The system of claim 1, further comprising: a third sensor configured to sense a selectable predetermined external condition.

7. The system of claim 6, wherein the selectable predetermined external condition includes an ambient temperature, a presence of an obstruction and a removal of the emergency assistance device.

8. The system of claim 1, wherein the first sensor is configured to couple with a module of the object.

9. The system of claim 1, wherein the central station further comprises: a database to store a location of the emergency equipment station.

10. The system of claim 1, wherein the central station is further configured to identify the location of the object to the at least one receiver.

11. The system of claim 1 wherein the signaling device of the emergency equipment station provides an audible signal.

12. The system of claim 1 wherein the signaling device of the emergency equipment station provides a visual signal.

* * * * *